(12) United States Patent
Hofmann et al.

(10) Patent No.: US 9,714,216 B2
(45) Date of Patent: Jul. 25, 2017

(54) USE OF URETHANE ALCOHOLS FOR PREPARATION OF POLYETHER POLYOLS

(71) Applicant: Covestro Deutschland AG, Leverkusen (DE)

(72) Inventors: Jörg Hofmann, Krefeld (DE); Kai Laemmerhold, Shanghai (CN); Hartmut Nefzger, Pulheim (DE); Monika Heinz, Köln (DE); Bert Klesczewski, Köln (DE); Klaus Lorenz, Dormagen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/036,486

(22) PCT Filed: Nov. 19, 2014

(86) PCT No.: PCT/EP2014/074987
§ 371 (c)(1),
(2) Date: May 13, 2016

(87) PCT Pub. No.: WO2015/075057
PCT Pub. Date: May 28, 2015

(65) Prior Publication Data
US 2016/0264519 A1 Sep. 15, 2016

(30) Foreign Application Priority Data

Nov. 22, 2013 (EP) .................................. 13194045

(51) Int. Cl.
| | |
|---|---|
| *C07C 269/06* | (2006.01) |
| *C08G 18/50* | (2006.01) |
| *C08G 18/71* | (2006.01) |
| *C08G 65/26* | (2006.01) |
| *C08G 65/333* | (2006.01) |
| *C08G 71/04* | (2006.01) |

(52) U.S. Cl.
CPC ........ *C07C 269/06* (2013.01); *C08G 18/5045* (2013.01); *C08G 18/711* (2013.01); *C08G 65/2603* (2013.01); *C08G 65/2606* (2013.01); *C08G 65/2615* (2013.01); *C08G 65/2618* (2013.01); *C08G 65/2663* (2013.01); *C08G 65/33344* (2013.01); *C08G 71/04* (2013.01)

(58) Field of Classification Search
CPC ............. C07C 269/06; C08G 65/2606; C08G 65/2618; C08G 65/2603; C08G 65/2615; C08G 65/33344; C08G 65/2663; C08G 18/711; C08G 71/04
See application file for complete search history.

(56) References Cited

U.S. PATENT DOCUMENTS

| | | | |
|---|---|---|---|
| 3,404,109 A | 10/1968 | Milgrom | |
| 3,538,043 A | 11/1970 | Herold | |
| 3,654,224 A | 4/1972 | Milgrom | |
| 3,829,505 A | 8/1974 | Herold | |
| 3,899,387 A * | 8/1975 | Freis .................. | C08G 18/4833 162/158 |
| 3,941,849 A | 3/1976 | Herold | |
| 4,263,408 A | 4/1981 | Meyborg et al. | |
| 4,355,188 A | 10/1982 | Herold et al. | |
| 4,500,704 A | 2/1985 | Kruper, Jr. et al. | |
| 4,663,472 A * | 5/1987 | Green .................... | C08G 71/04 560/115 |
| 4,721,818 A | 1/1988 | Harper et al. | |
| 4,877,906 A | 10/1989 | Harper | |
| 4,987,271 A | 1/1991 | Watabe et al. | |
| 5,001,210 A | 3/1991 | Coury et al. | |
| 5,032,671 A | 7/1991 | Harper | |
| 5,099,075 A | 3/1992 | Katz et al. | |
| 5,158,922 A | 10/1992 | Hinney et al. | |
| 5,391,722 A | 2/1995 | Chandalia et al. | |
| 5,470,813 A | 11/1995 | Le-Khac | |
| 6,646,100 B2 | 11/2003 | Hofmann et al. | |
| 6,767,986 B2 | 7/2004 | Moethrath et al. | |
| 6,780,813 B1 | 8/2004 | Hofmann et al. | |

(Continued)

FOREIGN PATENT DOCUMENTS

| | | |
|---|---|---|
| DE | 1 595 759 A1 | 3/1970 |
| DE | 3132258 A1 | 6/1982 |

(Continued)

OTHER PUBLICATIONS

International Search Report for PCT/EP2014/074987 mailed Mar. 18, 2015.

*Primary Examiner* — Shailendra Kumar
(74) *Attorney, Agent, or Firm* — K&L Gates LLP

(57) ABSTRACT

The present invention relates to a process for preparing polyether polyols by addition of alkylene oxides onto H-functional starter substances, characterized in that at least one urethane alcohol of formula (II) where $R^1$ is linear or branched $C_2$ to $C_{24}$-alkylene which may optionally be interrupted by heteroatoms such as O, S or N and may be substituted, $R^2$ is linear or branched $C_2$ to $C_{24}$-alkylene which may optionally be interrupted by heteroatoms such as O, S or N and may be substituted, R is H, linear or branched $C_1$ to $C_{24}$-alkyl, $C_3$ to $C_{24}$-cycloalkyl, $C_4$ to $C_{24}$-aryl, $C_5$ to $C_{24}$-aralkyl, $C_2$ to $C_{24}$-alkenyl, $C_2$ to $C_{24}$-alkynyl, each of which may optionally be interrupted by heteroatoms such as O, S or N and/or each of which may be substituted by alkyl, aryl and/or hydroxyl, is used as H-functional starter compound. The invention further provides the polyether polyols containing a urethane group, the polyether polyols obtainable by the process according to the invention, for the use of the inventive polyether polyols for preparation of a polyurethane polymer, and the resulting polyurethane polymers.

12 Claims, No Drawings

(56) References Cited

U.S. PATENT DOCUMENTS

| | | |
|---|---|---|
| 6,835,687 B2 | 12/2004 | Hofmann et al. |
| 7,008,900 B1 | 3/2006 | Hofmann et al. |
| 7,645,831 B2 | 1/2010 | Slark et al. |
| 8,946,466 B2 | 2/2015 | Gürtler et al. |
| 2009/0259012 A1* | 10/2009 | Roberts .............. C08G 18/0823 528/66 |

FOREIGN PATENT DOCUMENTS

| | | |
|---|---|---|
| EP | 0 007 502 A1 | 2/1980 |
| EP | 0 222 453 A2 | 5/1987 |
| EP | 385619 A2 | 9/1990 |
| EP | 406440 A1 | 1/1991 |
| EP | 0700949 A2 | 3/1996 |
| EP | 0743093 A1 | 11/1996 |
| EP | 0752415 A1 | 1/1997 |
| EP | 0761708 A2 | 3/1997 |
| EP | 1359177 A1 | 11/2003 |
| EP | 1 577 334 A1 | 9/2005 |
| GB | 1146660 A | 3/1969 |
| JP | 4145123 A | 5/1992 |
| WO | WO-97/29146 A1 | 8/1997 |
| WO | WO-97/40086 A1 | 10/1997 |
| WO | WO-98/03571 A1 | 1/1998 |
| WO | WO-98/16310 A1 | 4/1998 |
| WO | WO-99/14258 A1 | 3/1999 |
| WO | WO-00/47649 A1 | 8/2000 |
| WO | WO-01/39883 A1 | 6/2001 |
| WO | WO-01/80994 A1 | 11/2001 |
| WO | WO-2008/013731 A1 | 1/2008 |
| WO | WO-2011/144523 A1 | 11/2011 |

* cited by examiner

USE OF URETHANE ALCOHOLS FOR PREPARATION OF POLYETHER POLYOLS

CROSS-REFERENCE TO RELATED APPLICATIONS

This application is a national stage application (under 35 U.S.C. §371) of PCT/EP2014/074987, filed Nov. 19, 2014, which claims benefit of European Application No. 13194045.4, filed Nov. 22, 2013, both of which are incorporated herein by reference in their entirety.

The present invention relates to a process for preparing polyether polyols by addition of alkylene oxides onto H-functional starter compounds, characterized in that at least one urethane alcohol is used as H-functional starter compound. The invention further provides polyether polyols containing a urethane group, the polyether polyols obtainable by the process of the invention, the use of the polyether polyols of the invention for preparation of a polyurethane polymer, and the resulting polyurethane polymers.

BACKGROUND OF THE INVENTION

The preparation of polyether carbonate polyols by catalytic reaction of alkylene oxides (epoxides) and carbon dioxide in the presence of H-functional starter substances ("starters") has been the subject of intensive study for more than 40 years (e.g. Inoue et al., Copolymerization of Carbon Dioxide and Epoxide with Organometallic Compounds, Die Makromolekulare Chemie 130, 210-220, 1969). This reaction is shown in schematic form in scheme (I), where R is an organic radical such as alkyl, alkylaryl or aryl which may in each case also contain heteroatoms, for example O, S, Si, etc., and where e, f, g and b are each integers, and where the product shown here in scheme (I) for the polyether carbonate polyol should be understood as meaning merely that blocks having the structure shown may in principle be retained in the polyether carbonate polyol obtained but the sequence, number and length of the blocks and the OH functionality of the starter may vary and is not restricted to the polyether carbonate polyol shown in scheme (I). This reaction (see scheme (I)) is highly advantageous from an environmental standpoint since this reaction comprises converting a greenhouse gas such as $CO_2$ into a polymer. A further product formed, actually a by-product, is the cyclic carbonate shown in scheme (I) (for example propylene carbonate when $R=CH_3$, also referred to hereinafter as cPC, or ethylene carbonate when R=H, also referred to hereinafter as cEC).

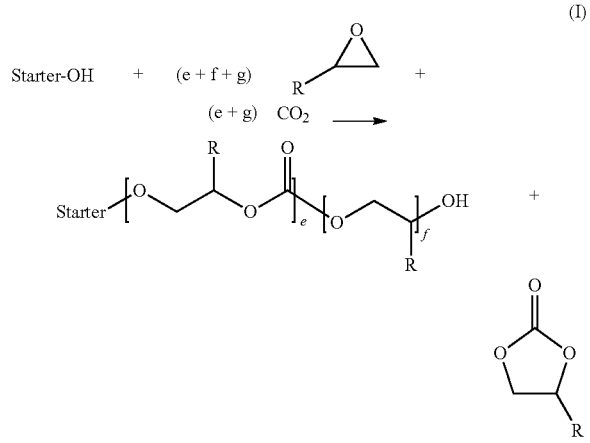

U.S. Pat. No. 3,829,505 and DE 1 595 759 describe the possibility of reacting OH-functional starter compounds in excess with aromatic polyisocyanates, in order to arrive in this way at polyurethane polyols containing OH groups and having at least 2 urethane groups, which can be used as starter oligomers for the DMC catalysis.

U.S. Pat. No. 3,654,224 describes the possibility of using amides, especially aromatic amides, for example benzamide, as starter compound for the DMC catalysis.

BRIEF SUMMARY OF THE INVENTION

It was therefore an object of the present invention to utilize the cyclic carbonate obtained as a by-product for the preparation of polyether polyols. Preferably, the polyether polyols thus obtainable are to be suitable for the preparation of polyurethanes, especially of flexible polyurethane foams.

This object is achieved in accordance with the invention by a process for preparing polyether polyols by addition of alkylene oxides onto H-functional starter compounds, characterized in that at least one urethane alcohol of formula (II)

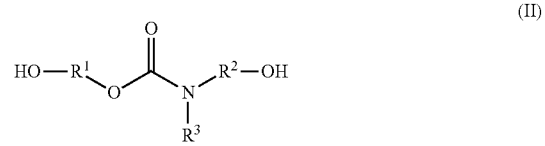

where
$R^1$ is linear or branched $C_2$- to $C_{24}$-alkylene which may optionally be interrupted by heteroatoms such as O, S or N and may be substituted, preferably $CH_2$—$CH_2$ or $CH_2$—$CH(CH_3)$,
$R^2$ is linear or branched $C_2$- to $C_{24}$-alkylene which may optionally be interrupted by heteroatoms such as O, S or N and may be substituted, preferably $CH_2$—$CH_2$ or $CH_2$—$CH(CH_3)$, and
$R^3$ is H, linear or branched $C_1$- to $C_{24}$-alkyl, $C_3$- to $C_{24}$-cycloalkyl, $C_4$- to $C_{24}$-aryl, $C_5$- to $C_{24}$-aralkyl, $C_2$- to $C_{24}$-alkenyl, $C_2$- to $C_{24}$-alkynyl, each of which may optionally be interrupted by heteroatoms such as O, S or N and/or each of which may be substituted by alkyl, aryl and/or hydroxyl, preferably H,
and where R1 to R3 may be identical or different, is used as H-functional starter compound.

The use of the word a in connection with countable parameters should be understood here and hereinafter to mean the number one only when this is evident from the context (for example through the wording "exactly one"). Otherwise, expressions such as "an alkylene oxide", "a urethane alcohol" etc. always refer to those embodiments in which two or more alkylene oxides, two or more urethane alcohols, etc. are used.

DETAILED DESCRIPTION OF THE INVENTION

The invention is illustrated in detail hereinafter. Various embodiments can be combined here with one another as desired, unless the opposite is apparent to the person skilled in the art from the context.

Preferably, the urethane alcohols of the formula (II) are obtainable by the reaction of cyclic carbonates with amino alcohols. Amino alcohols in the context of the invention are understood to mean compounds having at least one amino group and at least one OH group. Cyclic carbonates used are preferably those which are formed as by-products in the copolymerization of alkylene oxides with $CO_2$, examples being propylene carbonate (cPC) and ethylene carbonate (cEC).

Amino alcohols used are preferably those having primary or secondary amino groups, preferably primary amino groups, particular preference being given to using ethanolamine or isopropanolamine as the amino alcohol.

Preferably, the urethane alcohols of the formula (II) are obtainable by reacting propylene carbonate and/or ethylene carbonate with amino alcohols of formula (III)

where $R^2$ and $R^3$ are as defined above.

More preferably, the urethane alcohols of the formula (II) are obtainable by reacting propylene carbonate and/or ethylene carbonate with at least one amine selected from the group consisting of ethanolamine, diethanolamine, (N-methyl)ethanolamine, isopropanolamine, diisopropanolamine and propanolamine.

The reaction of the cyclic carbonates with the amino alcohols is effected preferably at 40 to 80° C., more preferably at 55 to 65° C. The reaction time is preferably 5 to 40 h, more preferably 10 to 30 h.

In a particularly advantageous embodiment, the cyclic carbonate is used in excess. Preferably, the molar ratio of cyclic carbonate to amino alcohol is 1.05 to 3, more preferably from 1.1 to 2, most preferably from 1.2 to 1.6. The excess cyclic carbonate can either be removed directly after the synthesis of the urethane alcohol by thin-film evaporation, for example, or can be left in the urethane alcohol and be used in the polyether polyol preparation as well. In the second case mentioned, the excess cyclic carbonate is removed from the product after the polyether polyol preparation.

As well as the urethane alcohols, it is additionally also possible to use H-functional starter compounds lacking urethane groups in the process of the invention, these being described hereinafter. Suitable H-functional starter substances ("starters") employed may be compounds having alkoxylation-active hydrogen atoms and having a molar mass of 18 to 4500 g/mol, preferably of 62 to 500 g/mol and more preferably of 62 to 182 g/mol. The ability to use a starter having a low molar mass is a distinct advantage over the use of oligomeric starters prepared by means of a prior alkoxylation. In particular, a level of economic viability is achieved that is made possible by the omission of a separate alkoxylation process.

Groups active in respect of the alkoxylation and having active hydrogen atoms are, for example, —OH, —$NH_2$ (primary amines), —NH— (secondary amines), —SH, and —$CO_2H$, preferably —OH and $NH_2$, more preferably —OH. H-Functional starter substances used are, for example, one or more compounds selected from the group consisting of mono- and polyhydric alcohols, polyfunctional amines, polyfunctional thiols, amino alcohols, thio alcohols, hydroxy esters, polyether polyols, polyester polyols, polyester ether polyols, polyether carbonate polyols, polycarbonate polyols, polycarbonates, polyethyleneimines, polyetheramines, polytetrahydrofurans (e.g. PolyTHF® from BASF), polytetrahydrofuran amines, polyether thiols, polyacrylate polyols, castor oil, the mono- or diglyceride of castor oil, monoglycerides of fatty acids, chemically modified mono-, di- and/or triglycerides of fatty acids, and $C_1$-$C_{24}$ alkyl fatty acid esters containing an average of at least 2 OH groups per molecule. By way of example, the $C_1$-$C_{24}$-alkyl fatty acid esters containing an average of at least 2 OH groups per molecule are commercial products such as Lupranol Balance® (from BASF AG), Merginol® products (from Hobum Oleochemicals GmbH), Sovermol® products (from Cognis Deutschland GmbH & Co. KG) and Soyol® TM products (from USSC Co.). Monofunctional starter substances used may be alcohols, amines, thiols and carboxylic acids. Monofunctional alcohols used may be: methanol, ethanol, 1-propanol, 2-propanol, 1-butanol, 2-butanol, tert-butanol, 3-buten-1-ol, 3-butyn-1-ol, 2-methyl-3-buten-2-ol, 2-methyl-3-butyn-2-ol, propargyl alcohol, 2-methyl-2-propanol, 1-tert-butoxy-2-propanol, 1-pentanol, 2-pentanol, 3-pentanol, 1-hexanol, 2-hexanol, 3-hexanol, 1-heptanol, 2-heptanol, 3-heptanol, 1-octanol, 2-octanol, 3-octanol, 4-octanol, phenol, 2-hydroxybiphenyl, 3-hydroxybiphenyl, 4-hydroxybiphenyl, 2-hydroxypyridine, 3-hydroxypyridine, 4-hydroxypyridine. Useful monofunctional amines include: butylamine, tert-butylamine, pentylamine, hexylamine, aniline, aziridine, pyrrolidine, piperidine, morpholine. Monofunctional thiols used may be: ethanethiol, 1-propanethiol, 2-propanethiol, 1-butanethiol, 3-methyl-1-butanethiol, 2-butene-1-thiol, thiophenol. Monofunctional carboxylic acids include: formic acid, acetic acid, propionic acid, butyric acid, fatty acids such as stearic acid, palmitic acid, oleic acid, linoleic acid, linolenic acid, benzoic acid, acrylic acid.

Polyhydric alcohols suitable as H-functional starter substances are, for example, dihydric alcohols (for example ethylene glycol, diethylene glycol, propylene glycol, dipropylene glycol, 1,3-propanediol, 1,4-butanediol, 1,4-butenediol, 1,4-butynediol, neopentyl glycol, 1,5-pentanediol, methylpentanediols (for example 3-methyl-1,5-pentanediol), 1,6-hexanediol, 1,8-octanediol, 1,10-decanediol, 1,12-dodecanediol, bis(hydroxymethyl)cyclohexanes (for example 1,4-bis(hydroxymethyl)cyclohexane), triethylene glycol, tetraethylene glycol, polyethylene glycols, dipropylene glycol, tripropylene glycol, polypropylene glycols, dibutylene glycol and polybutylene glycols); trihydric alcohols (for example trimethylolpropane, glycerol, trishydroxyethyl isocyanurate, castor oil); tetrahydric alcohols (for example pentaerythritol); polyalcohols (for example sorbitol, hexitol, sucrose, starch, starch hydrolyzates, cellulose, cellulose hydrolyzates, hydroxy-functionalized fats and oils, especially castor oil), and all the modification products of these aforementioned alcohols with different amounts of ε-caprolactone.

The H-functional starter substances may also be selected from the substance class of the polyether polyols having a molecular weight $M_n$ in the range from 18 to 4500 g/mol and a functionality of 2 to 3. Preference is given to polyether polyols formed from repeat ethylene oxide and propylene oxide units, preferably having a proportion of propylene oxide units of 35% to 100%, particularly preferably having a proportion of propylene oxide units of 50% to 100%. These may be random copolymers, gradient copolymers, alternating copolymers or block copolymers of ethylene oxide and propylene oxide. More particularly, polyether polyols obtainable by the process according to the invention described here are used. For this purpose, these polyether polyols used as H-functional starter substances are prepared in a separate reaction step beforehand.

The H-functional starter substances may also be selected from the substance class of the polyester polyols. The polyester polyols used are at least difunctional polyesters. Preferably, polyester polyols consist of alternating acid and alcohol units. Acid components used are, for example, succinic acid, maleic acid, maleic anhydride, adipic acid, phthalic anhydride, phthalic acid, isophthalic acid, terephthalic acid, tetrahydrophthalic acid, tetrahydrophthalic anhydride, hexahydrophthalic anhydride or mixtures of the acids and/or anhydrides mentioned. Alcohol components used are, for example, ethanediol, propane-1,2-diol, propane-1,3-diol, butane-1,4-diol, pentane-1,5-diol, neopentyl glycol, hexane-1,6-diol, 1,4-bis(hydroxymethyl)cyclohexane, diethylene glycol, dipropylene glycol, trimethylolpropane, glycerol, pentaerythritol or mixtures of the alcohols mentioned. Employing dihydric or polyhydric polyether polyols as the alcohol component affords polyester ether polyols which can likewise serve as starter substances for preparation of the polyether carbonate polyols. In addition, H-functional starter substances used may be polycarbonate diols which are prepared, for example, by reaction of phosgene, dimethyl carbonate, diethyl carbonate or diphenyl carbonate and difunctional alcohols or polyester polyols or polyether polyols. Examples of polycarbonates may be found, for example, in EP-A 1359177.

In a further embodiment of the invention, it is possible to use polyether carbonate polyols as H-functional starter substances.

The H-functional starter substances generally have a functionality (i.e. the number of hydrogen atoms active in respect of the polymerization per molecule) of 1 to 8, preferably of 2 or 3. The H-functional starter substances are used either individually or as a mixture of at least two H-functional starter substances.

More preferably, the H-functional starter substances are one or more compounds selected from the group consisting of ethylene glycol, propylene glycol, propane-1,3-diol, butane-1,3-diol, butane-1,4-diol, pentane-1,5-diol, 2-methylpropane-1,3-diol, neopentyl glycol, hexane-1,6-diol, octane-1,8-diol, diethylene glycol, dipropylene glycol, glycerol, trimethylolpropane, pentaerythritol, sorbitol and polyether polyols having a molecular weight Mn in the range from 150 to 4500 g/mol and a functionality of 2 to 3.

The invention further provides polyether polyols containing a structural unit of the formula (IV)

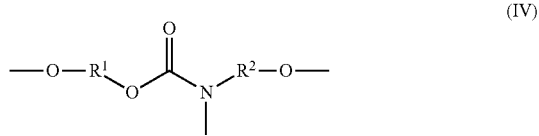

where $R^1$ and $R^2$ are as defined above. Preferably, the polyether polyols of the invention contain exactly one single structural unit of the formula (IV) per polyether polyol molecule.

The polyether polyols of the invention preferably have an OH number of 3 to 400 mg KOH/g, more preferably 10 to 200 mg KOH/g.

In addition, the polyether polyols of the invention have a functionality of 2.0 to 3.0, preferably of 2.5 to 2.95.

The present invention further provides a process for preparing polyether polyols by adding alkylene oxides onto H-functional starter compounds, characterized in that at least one urethane alcohol of formula (II) is used as H-functional starter compound and the addition is effected in the presence of at least one double metal cyanide catalyst (also referred to as DMC catalyst).

DMC catalysts suitable for the process of the invention are known in principle from the prior art (see, for example, U.S. Pat. No. 3,404,109, U.S. Pat. No. 3,829,505, U.S. Pat. No. 3,941,849 and U.S. Pat. No. 5,158,922). DMC catalysts which are described, for example, in U.S. Pat. No. 5,470,813, EP-A-0 700 949, EP-A-0 743 093, EP-A-0 761 708, WO 97/40086, WO 98/16310 and WO 00/47649 have a very high activity in the polymerization of alkylene oxides and, in some cases, the copolymerization of alkylene oxides with suitable comonomers, for example lactones, cyclic carboxylic anhydrides, lactides, cyclic carbonates or carbon dioxide, and enable the preparation of polymeric polyols at very low catalyst concentrations (25 ppm or less), such that there is generally no longer any need to separate the catalyst from the finished product. A typical example is that of the highly active DMC catalysts which are described in EP-A-0 700 949 and contain not only a double metal cyanide compound (e.g. zinc hexacyanocobaltate(III)) and an organic complex ligand (e.g. tert-butanol) but also a polyether having a number-average molecular weight greater than 500 g/mol.

It is also possible to use the alkaline DMC catalysts disclosed in WO 2011/144523.

Cyanide-free metal salts suitable for preparation of the double metal cyanide compounds preferably have the general formula (V)

$$M(X)_n \qquad (V)$$

where
M is selected from the metal cations $Zn^{2+}$, $Fe^{2+}$, $Ni^{2+}$, $Mn^{2+}$, $Co^{2+}$, $Sr^{2+}$, $Sn^{2+}$, $Pb^{2+}$ and $Cu^{2+}$;
M is preferably $Zn^{2+}$, $Fe^{2+}$, $Co^{2+}$ or $Ni^{2+}$,
X is one or more (i.e. different) anions, preferably an anion selected from the group of the halides (i.e. fluoride, chloride, bromide, iodide), hydroxide, sulfate, carbonate, cyanate, thiocyanate, isocyanate, isothiocyanate, carboxylate, oxalate and nitrate;
n is 1 when X=sulfate, carbonate or oxalate and
n is 2 when X=halide, hydroxide, cyanate, thiocyanate, isocyanate, isothiocyanate or nitrate;
or suitable cyanide-free metal salts have the general formula (VI)

$$M_r(X)_3 \qquad (VI)$$

where
M is selected from the metal cations $Fe^{3+}$, $Al^{3+}$ and $Cr^{3+}$,
X is one or more (i.e. different) anions, preferably an anion selected from the group of the halides (i.e. fluoride, chloride, bromide, iodide), hydroxide, sulfate, carbonate, cyanate, thiocyanate, isocyanate, isothiocyanate, carboxylate, oxalate and nitrate;
r is 2 when X=sulfate, carbonate or oxalates and
r is 1 when X=halide, hydroxide, cyanate, thiocyanate, isocyanate, isothiocyanate, carboxylate or nitrate,
or suitable cyanide-free metal salts have the general formula (VII)

$$M(X)_s \qquad (VII)$$

where
M is selected from the metal cations $Mo^{4+}$, $V^{4+}$ and $W^{4+}$,
X is or more (i.e. different) anions, preferably an anion selected from the group of the halides (i.e. fluoride, chloride, bromide, iodide), hydroxide, sulfate, carbonate, cyanate, thiocyanate, isocyanate, isothiocyanate, carboxylate, oxalate and nitrate;
s is 2 when X=sulfate, carbonate or oxalate and
s is 4 when X=halide, hydroxide, cyanate, thiocyanate, isocyanate, isothiocyanate, carboxylate or nitrate,
or suitable cyanide-free metal salts have the general formula (VIII)

$$M(X)_t \qquad (VIII)$$

where

M is selected from the metal cations $Mo^{6+}$ and $W^{6+}$,

X is one or more (i.e. different) anions, preferably an anion selected from the group of the halides (i.e. fluoride, chloride, bromide, iodide), hydroxide, sulfate, carbonate, cyanate, thiocyanate, isocyanate, isothiocyanate, carboxylate, oxalate and nitrate;

t is 3 when X=sulfate, carbonate or oxalate and t is 6 when X=halide, hydroxide, cyanate, thiocyanate, isocyanate, isothiocyanate, carboxylate or nitrate.

Examples of suitable cyanide-free metal salts are zinc chloride, zinc bromide, zinc iodide, zinc acetate, zinc acetylacetonate, zinc benzoate, zinc nitrate, iron(II) sulfate, iron (II) bromide, iron(II) chloride, cobalt(II) chloride, cobalt(III) thiocyanate, nickel(II) chloride and nickel(II) nitrate. It is also possible to use mixtures of different metal salts.

Metal cyanide salts suitable for preparation of the double metal cyanide compounds preferably have the general formula (IX)

$(Y)_aM'(CN)_b(A)_c$ (IX)

where

M' is selected from one or more metal cations from the group consisting of Fe(II), Fe(III), Co(II), Co(III), Cr(II), Cr(III), Mn(II), Mn(II), Ir(III), Ni(II), Rh(III), Ru(II), V(IV) and V(V); M' is preferably one or more metal cations from the group consisting of Co(II), Co(III), Fe(II), Fe(III), Cr(III), Ir(III) and Ni(II), Y is selected from one or more metal cations from the group consisting of alkali metal (i.e. $Li^+$, $Na^+$, $K^+$, $Rb^+$, $Cs^+$) and alkaline earth metal (i.e. $Be^{2+}$, $Ca^{2+}$, $Mg^{2+}$, $Sr^{2+}$, $Ba^2$), A is selected from one or more anions of the group consisting of halides (i.e. fluoride, chloride, bromide, iodide), hydroxide, sulfate, carbonate, cyanate, thiocyanate, isocyanate, isothiocyanate, carboxylate, oxalate or nitrate and a, b and c are integers, the values for a, b and c being selected such as to ensure the electronic neutrality of the metal cyanide salt; a is preferably 1, 2, 3 or 4; b is preferably 4, 5 or 6; c preferably has the value 0.

Examples of suitable metal cyanide salts are potassium hexacyanocobaltate(III), potassium hexacyanoferrate(II), potassium hexacyanoferrate(III), calcium hexacyanocobaltate(III) and lithium hexacyanocobaltate(III).

Preferred double metal cyanide compounds present in the DMC catalysts are compounds of general formula (X)

$M_x[M'_{x'}(CN)_y]_z$ (X)

in which M is defined as in formula (V) to (VIII) and

M' is as defined in formula (IX), and x, x', y and z are integers and are chosen so as to ensure electronic neutrality of the double metal cyanide compound.

Preferably, x=3, x'=1, y=6 and z=2,

M=Zn(II), Fe(II), Co(II) or Ni(II) and

M'=Co(III), Fe(III), Cr(III) or Ir(III).

Examples of suitable double metal cyanide compounds are zinc hexacyanocobaltate(III), zinc hexacyanoiridate(III), zinc hexacyanoferrate(III) and cobalt(II) hexacyanocobaltate(III). Further examples of suitable double metal cyanide compounds can be found, for example, in U.S. Pat. No. 5,158,922 (column 8, lines 29-66). Particular preference is given to using zinc hexacyanocobaltate(II).

The organic complex ligands added in the preparation of the DMC catalysts are disclosed, for example, in U.S. Pat. No. 5,158,922 (see especially column 6 lines 9 to 65), U.S. Pat. No. 3,404,109, U.S. Pat. No. 3,829,505, U.S. Pat. No. 3,941,849, EP-A-0 700 949, EP-A-0 761 708, JP-A-4145123, U.S. Pat. No. 5,470,813, EP-A-0 743 093 and WO-A-97/40086. The organic complex ligands used are, for example, water-soluble organic compounds containing heteroatoms such as oxygen, nitrogen, phosphorus or sulfur, which can form complexes with the double metal cyanide compound. Preferred organic complex ligands are alcohols, aldehydes, ketones, ethers, esters, amides, ureas, nitriles, sulfides and mixtures thereof. Particularly preferred organic complex ligands are aliphatic ethers (such as dimethoxyethane), water-soluble aliphatic alcohols (such as ethanol, isopropanol, n-butanol, isobutanol, sec-butanol, tert-butanol, 2-methyl-3-buten-2-ol and 2-methyl-3-butyn-2-ol), compounds which contain both aliphatic or cycloaliphatic ether groups and aliphatic hydroxyl groups (for example ethylene glycol mono-tert-butyl ether, diethylene glycol mono-tert-butyl ether, tripropylene glycol monomethyl ether and 3-methyl-3-oxetanemethanol). Extremely preferred organic complex ligands are selected from one or more compounds of the group consisting of dimethoxyethane, tert-butanol 2-methyl-3-buten-2-ol, 2-methyl-3-butyn-2-ol, ethylene glycol mono-tert-butyl ether and 3-methyl-3-oxetanemethanol.

Optionally used in the preparation of the DMC catalysts are one or more complex-forming component(s) from the compound classes of the polyethers, polyesters, polycarbonates, polyalkylene glycol sorbitan esters, polyalkylene glycol glycidyl ethers, polyacrylamide, poly(acrylamide-co-acrylic acid), polyacrylic acid, poly(acrylic acid-co-maleic acid), polyacrylonitrile, polyalkyl acrylates, polyalkyl methacrylates, polyvinyl methyl ethers, polyvinyl ethyl ethers, polyvinyl acetate, polyvinyl alcohol, poly-N-vinylpyrrolidone, poly(N-vinylpyrrolidone-co-acrylic acid), polyvinyl methyl ketone, poly(4-vinylphenol), poly(acrylic acid-co-styrene), oxazoline polymers, polyalkyleneimines, maleic acid and maleic anhydride copolymers, hydroxyethyl cellulose and polyacetals, or of the glycidyl ethers, glycosides, carboxylic esters of polyhydric alcohols, gallic acids or salts, esters or amides thereof, cyclodextrins, phosphorus compounds, α,β-unsaturated carboxylic esters or ionic surface- or interface-active compounds.

Preferably, in the preparation of the DMC catalysts, in the first step, the aqueous solutions of the metal salt (e.g. zinc chloride), used in a stoichiometric excess (at least 50 mol %) based on metal cyanide salt (i.e. at least a molar ratio of cyanide-free metal salt to metal cyanide salt of 2.25:1.00), and the metal cyanide salt (e.g. potassium hexacyanocobaltate) are converted in the presence of the organic complex ligand (e.g. tert-butanol), such that a suspension is formed comprising the double metal cyanide compound (e.g. zinc hexacyanocobaltate), water, excess cyanide-free metal salt, and the organic complex ligands. This organic complex ligand may be present in the aqueous solution of the cyanide-free metal salt and/or of the metal cyanide salt, or it is added directly to the suspension obtained after precipitation of the double metal cyanide compound. It has been found to be advantageous to mix the aqueous solutions of the cyanide-free metal salt and of the metal cyanide salt and the organic complex ligands by stirring vigorously. Optionally, the suspension formed in the first step is subsequently treated with a further complex-forming component. The complex-forming component is preferably used in a mixture with water and organic complex ligand. A preferred process for performing the first step (i.e. the preparation of the suspension) comprises using a mixing nozzle, particularly preferably using a jet disperser, as described in WO-A-01/39883.

In the second step, the solid (i.e. the precursor of the inventive catalyst) is isolated from the suspension by known techniques, such as centrifugation or filtration.

In a preferred execution variant for preparing the catalyst, the isolated solid is subsequently washed in a third process step with an aqueous solution of the organic complex ligand (for example by resuspension and subsequent reisolation by filtration or centrifugation). In this way, it is possible to remove, for example, water-soluble by-products such as potassium chloride from the catalyst. Preferably, the amount of the organic complex ligand in the aqueous wash solution is between 40% and 80% by weight, based on the overall solution. Further complex-forming component is optionally added to the aqueous wash solution in the third step, preferably in the range between 0.5% and 5% by weight, based on the overall solution.

It is moreover advantageous to wash the isolated solid more than once. For this purpose, for example, the first washing procedure can be repeated. It is preferable, however, to use non-aqueous solutions for further washing operations, e.g. a mixture of organic complex ligands and other complex-forming components.

The isolated and optionally washed solid is subsequently, optionally after pulverization, dried at temperatures of generally 20-100° C. and at pressures of generally 0.1 mbar to standard pressure (1013 mbar).

A preferred process for isolating the DMC catalysts from the suspension by filtration, filtercake washing and drying is described in WO-A-01/80994.

The concentration of DMC catalyst used is 5.0 ppm to 1000 ppm, preferably 10 ppm to 900 ppm and more preferably 20 ppm to 80 ppm, based on the mass of the polyether polyol to be prepared. According to the profile of requirements for the downstream use, the DMC catalyst can be left in the product or (partly) removed. The (partial) removal of the DMC catalyst can be effected, for example, by treatment with adsorbents. Methods of removing DMC catalysts are described, for example, in U.S. Pat. No. 4,987,271, DE-A-3132258, EP-A-0 406 440, U.S. Pat. No. 5,391,722, U.S. Pat. No. 5,099,075, U.S. Pat. No. 4,721,818, U.S. Pat. No. 4,877,906 and EP-A-0 385 619.

Alkylene oxides suitable for the process of the invention have 2 to 24 carbon atoms. The alkylene oxides having 2 to 24 carbon atoms are preferably one or more compounds selected from the group consisting of ethylene oxide, propylene oxide, I-butene oxide, 2,3-butene oxide, 2-methyl-1,2-propene oxide (isobutene oxide), 1-pentene oxide, 2,3-pentene oxide, 2-methyl-1,2-butene oxide, 3-methyl-1,2-butene oxide, 1-hexene oxide, 2,3-hexene oxide, 3,4-hexene oxide, 2-methyl-1,2-pentene oxide, 4-methyl-1,2-pentene oxide, 2-ethyl-1,2-butene oxide, 1-heptene oxide, 1-octene oxide, 1-nonene oxide, 1-decene oxide, 1-undecene oxide, 1-dodecene oxide, 4-methyl-1,2-pentene oxide, butadiene monoxide, isoprene monoxide, cyclopentene oxide, cyclohexene oxide, cycloheptene oxide, cyclooctene oxide, styrene oxide, methylstyrene oxide, pinene oxide, mono- or polyalkylene oxidized fats as mono-, di- and triglycerides, alkylene oxidized fatty acids, $C_1$-$C_{24}$ esters of alkylene oxidized fatty acids, epichlorohydrin, glycidol, and derivatives of glycidol, for example methyl glycidyl ether, ethyl glycidyl ether, 2-ethylhexyl glycidyl ether, allyl glycidyl ether, and alkylene oxide-functional alkyloxysilanes, for example 3-glycidyloxypropyltrimethoxysilane, 3-glycidyloxypropyltriethoxysilane, 3-glycidyloxypropyltripropoxysilane, 3-glycidyloxypropylmethyldimethoxysilane, 3-glycidyloxypropylethyldiethoxysilane and 3-glycidyloxypropyltriisopropoxysilane. The alkylene oxide used is preferably at least one alkylene oxide selected from the group consisting of ethylene oxide and propylene oxide. Further monomers copolymerizable with alkylene oxides by the process of the invention under DMC catalysis are all oxygen-containing cyclic compounds, especially lactones, lactides, aliphatic and aromatic cyclic carboxylic anhydrides and cyclic carbonates. The use thereof is described in U.S. Pat. No. 3,538,043, U.S. Pat. No. 4,500,704, U.S. Pat. No. 5,032,671, U.S. Pat. No. 6,646,100, EP-A-0 222 453 and WO-A-2008/013731.

A number of variants for performance of the process of the invention are described in detail hereinafter. The illustration is merely by way of example and should not be understood such that it restricts the present invention.

In a preferred embodiment of the invention (variant A), at least one urethane alcohol of the formula (II) and the double metal cyanide catalyst are first initially charged and then the alkylene oxide is added.

Variant A) ("Semi-Batchwise Procedure"):

In variant A) of the process of the invention, at least one urethane alcohol of the formula (II) is first initially charged together with the DMC catalyst in a reactor/reactor system. It is optionally possible to add small amounts of an inorganic mineral acid, preferably phosphoric acid, to the urethane alcohol prior to contacting with the DMC catalyst, as described in applications WO-A-99/14258 and EP-A-1 577 334, in order to neutralize any traces of base in the urethane alcohol, or in order to generally stabilize the production process. After heating to temperatures of 50° C. to 160° C., preferably 60° C. to 140° C., most preferably 70° C. to 140° C., in a preferred process variant, the reactor contents are stripped with inert gas while stirring over a period of preferably 10 to 60 min. In the course of stripping with inert gas, volatile constituents, for example traces of water, are removed with introduction of inert gases into the liquid phase with simultaneous application of reduced pressure, at an absolute pressure of 5 mbar to 500 mbar. After metered addition of typically 5% by weight to 20% by weight of one or more alkylene oxides, based on the amount of urethane alcohol initially charged, the DMC catalyst is activated. The addition of one or more alkylene oxides may precede, coincide with or follow the heating of the reactor contents to temperatures of 50° C. to 160° C., preferably 60° C. to 140° C., most preferably 70° C. to 140° C.; it preferably follows after the stripping. The activation of the catalyst is noticeable by an accelerated drop in the reactor pressure, which indicates the commencement of alkylene oxide conversion. The desired amount of alkylene oxide or alkylene oxide mixture can then be supplied continuously to the reaction mixture, and a reaction temperature of 20° C. to 200° C., preferably of 50° C. to 160° C., more preferably 70° C. to 150° C., most preferably 80° C. to 140° C., is chosen. The reaction temperature is in many cases identical to the activation temperature; alternatively, it can be altered on completion of catalyst activation, for example in order not to subject sensitive starter compounds to excessive thermal stress. It is often the case that catalyst activation is effected so quickly that the metered addition of a separate amount of alkylene oxide for catalyst activation can be dispensed with and it is possible to commence directly, optionally at first with a reduced metering rate, with the continuous metered addition of one or more alkylene oxides. The reaction temperature may also be varied within the limits described over the entire alkylene oxide metering phase. The alkylene oxides can likewise be supplied to the reactor in different ways: one option is metered addition into the gas phase or directly into the liquid phase, for example by means of an immersed tube or a distributor ring close to the reactor base in a zone with good mixing. In the case of DMC-catalyzed processes, metered addition in the liquid phase is frequently the preferred variant. The one or more alkylene oxide(s) should be fed continuously to the reactor in such a way that the safety-related pressure limits of the reactor system used are not exceeded. Especially in the case of metered co-addition of ethylene oxide-containing alkylene oxide mixtures or pure ethylene oxide, it should be ensured that a sufficient partial inert gas pressure is maintained within the reactor during the startup and metering phase. This can be established, for example, by means of noble gases or nitrogen. In the case of metered addition into the liquid phase, the metering units should be designed such that they self-empty, for example through provision of metering holes on the underside of the distributor ring. Generally, apparatus measures, for example the installation of non-return valves, should prevent backflow of reaction medium into the metering units and reactant reservoirs. If an alkylene oxide mixture is being metered in, the respective alkylene oxides can be supplied to the reactor separately or as a mixture. Premixing of the alkylene oxides with one another can be achieved, for example, by means of a mixing unit present in the common metering zone ("inline blending"). It has also been found to be useful to meter the alkylene oxides, on the pump pressure side, individually or in premixed form into a pumped circulation system conducted, for example, through one or more heat exchangers. In that case, for good mixing with the reaction medium, it is advantageous to integrate a high-shear mixing unit into the alkylene oxide/reaction medium stream. The temperature of the exothermic ring-opening addition reaction is kept at the desired level by cooling. According to the prior art relating to design of polymerization reactors for exothermic reactions (for example Ullmann's Encyclopedia of Industrial Chemistry, vol. B4, pp. 167 ff., 5th ed., 1992), such cooling is generally effected via the reactor wall (e.g. jacket, half-coil pipe) and by means of further heat exchange surfaces disposed internally in the reactor and/or externally in the pumped circulation system, for example in cooling coils, cooling cartridges, or plate, shell-and-tube or mixer heat exchangers. This cooling should be designed such that effective cooling is possible even on commencement of the metering phase, i.e. with a low fill level.

Generally, good mixing of the reactor contents should be ensured in all reaction phases through design and use of standard stirring units, suitable stirring units here being especially stirrers arranged over one or more levels or stirrer types which act over the full fill height, for example gate stirrers (see, for example, Handbuch Apparate [Apparatus Handbook]; Vulkan-Verlag Essen, 1st ed. (1990), p. 188-208). Of particular technical relevance here is a specific mixing power which is introduced on average over the entire reactor contents and is generally in the range from 0.2 W/L to 5 W/L, based on the reactor volume, with correspondingly higher local power inputs in the region of the stirrer units themselves and possibly in the case of relatively low fill levels. In order to achieve optimal stirring action, combinations of baffles (for example flat or tubular baffles) and cooling coils (or cooling cartridges) may be arranged within the reactor according to the general prior art, and these may also extend over the vessel base. The stirring power of the mixing unit may also be varied as a function of the fill level during the metering phase, in order to ensure a particularly high energy input in critical reaction phases. Preference is given to using stirrer units with stirrer levels close to the base. In addition, the stirrer geometry should contribute to reducing the foaming of reaction products. The foaming of reaction mixtures can be observed, for example, after the end of the metering and post-reaction phase, when residual alkylene oxides are additionally removed under reduced pressure, at absolute pressures in the range from 1 mbar to 500 mbar. For such cases, suitable stirrer units have been found to be those which achieve continuous mixing of the liquid surface. According to the requirement, the stirrer shaft has a base bearing and optionally further support bearings in the vessel. The stirrer shaft can be driven from the top or bottom (with central or eccentric arrangement of the shaft).

Alternatively, it is also possible to achieve the necessary mixing exclusively by means of a pumped circulation system conducted through a heat exchanger, or to operate this pumped circulation system as a further mixing component in addition to the stirrer unit, in which case the reactor contents are pumped in circulation as required (typically 1 to 50 times per hour). The specific mixing energy introduced by means of pumped circulation, for example by means of an external heat exchanger or, in the case of recycling into the reactor, by means of a nozzle or injector, likewise amounts to values averaging from 0.2 to 5 W/L, this being based on the liquid volume present in the reactor and the pumped circulation system at the end of the reaction phase.

A wide variety of different reactor types is suitable for the performance of the process of the invention. Preference is given to using cylindrical vessels having a height/diameter ratio of 1.0:1 to 10:1. Useful reactor bases include hemispherical, dished, flat or conical bases.

The end of the metered addition of the one or more alkylene oxides may be followed by a postreaction phase in which residual alkylene oxide is depleted. The end of this postreaction phase has been attained when no further pressure drop can be detected in the reaction tank.

Traces of unreacted alkylene oxides, after the reaction phase, can optionally be removed quantitatively under reduced pressure, at an absolute pressure of 1 mbar to 500 mbar, or by stripping. Stripping removes volatile constituents, for example (residual) alkylene oxides, with introduction of inert gases or steam into the liquid phase with simultaneous application of reduced pressure, for example by passing inert gas through at an absolute pressure of 5 mbar to 500 mbar. The removal of volatile constituents, for example of unconverted alkylene oxides, either under reduced pressure or by stirring, is effected at temperatures of 20° C. to 200° C., preferably at 50° C. to 160° C., and preferably with stirring. Such stripping operations can also be performed in what are called stripping columns, in which an inert gas or steam stream is passed counter to the product stream. Preference is given to performing the stripping operation with inert gases in the absence of steam.

After constant pressure has been attained or after volatile constituents have been removed by reduced pressure and/or stripping, the product obtained by the process of the invention can be discharged from the reactor.

A characteristic of DMC catalysts is their marked sensitivity to high concentrations of hydroxyl groups which are caused in standard industrial scale processes for polyether polyol production, for example, by high proportions of starters such as ethylene glycol, propylene glycol, glycerol, trimethylolpropane, sorbitol or sucrose that are present in the reaction mixture at the start of the reaction, and polar impurities in the reaction mixture or the starter(s). In that case, the DMC catalysts cannot be converted to the polymerization-active form during the reaction initiation phase. Impurities may, for example, be water, compounds having a high number of hydroxyl groups closely adjacent to one another, such as carbohydrates and carbohydrate derivatives, or compounds having basic groups, for example amines. For the process of the invention, it is of particular significance that even substances having urethane groups adjacent to hydroxyl groups do not have an adverse effect on the catalyst activity. In order nevertheless to be able to subject starters having a high concentration of OH groups, or starters having impurities considered to be catalyst poisons, or starters having arrangements of functional groups that have a disadvantageous effect on catalyst activity, to DMC-catalyzed alkylene oxide addition reactions, the hydroxyl group concentration has to be lowered, the starter concentration has to be reduced, and the catalyst poisons have to be rendered harmless. For this purpose, for example, it is possible first to use these starter compounds to prepare, by means of basic catalysis, prepolymers which, after workup, are then converted by means of DMC catalysis to the desired alkylene oxide addition products of high molar mass. A disadvantage of this procedure is that such prepolymers often obtained by means of basic catalysis have to be worked up very carefully, in order to rule out deactivation of the DMC catalyst by traces of basic catalyst entrained by the prepolymers.

These disadvantages can be overcome by the method of continuous metered addition of starter, which is disclosed in WO-A-97/29146. In this case, critical compounds are not initially charged in the reactor but supplied continuously to the reactor during the reaction in addition to the alkylene oxides. Starting media, or what are called H-functional starter polyols S-I, for the reaction which may be initially charged in this process are alkylene oxide addition products of H-functional starter compounds, for example including those without urethane groups. It is also possible to use the polyether polyol prepared by the process of the invention itself, which has been prepared separately beforehand, as the starting medium (S-I). There is thus no need to first separately prepare prepolymers suitable for further alkylene oxide additions.

Variant B) ("CAOS Semi-Batchwise Procedure"):

In variant B) of the process of the invention, an H-functional starter polyol S-I and the DMC catalyst are initially charged in the reactor system, and at least one urethane alcohol of the formula (II) is fed in continuously together with one or more alkylene oxides. Suitable H-functional starter polyols S-I for this variant are alkylene oxide addition products, for example polyether polyols, polycarbonate polyols, polyestercarbonate polyols or polyethercarbonate polyols, each, for example, with OH numbers in the range from 3.0 mg KOH/g to 1000 mg KOH/g, preferably from 3.0 mg KOH/g to 300 mg KOH/g, and/or a polyether polyol prepared separately by the process of the invention. Preference is given to using a polyether polyol prepared separately by the process of the invention as H-functional starter polyol S-I.

The metered addition of the at least one urethane alcohol and the one or more alkylene oxide(s) is preferably ended simultaneously, or the urethane alcohol and a first portion of one or more alkylene oxide(s) are first metered in together and then the second portion of one or more alkylene oxides is metered in, the sum total of the first and second portions of one or more alkylene oxides corresponding to the total amount of the one or more alkylene oxides used. The first portion is preferably 60% by weight to 98% by weight and the second portion is 40% by weight to 2% by weight of the total amount of one or more alkylene oxides to be metered in. If the composition of the alkylene oxide metering stream is altered after the end of the metered addition of the urethane alcohol, it is also possible to prepare products having multiblock structures by process variant B). The metered addition of the reagents may be followed by a postreaction phase in which the consumption of alkylene oxide can be quantified by monitoring the pressure. On attainment of constant pressure, optionally after application of reduced pressure or by stripping to remove unconverted alkylene oxides, as described above, the product can be discharged.

It is alternatively also possible, in variant B of the process of the invention, in addition to the urethane alcohol, also to use the above-described H-functional starter compounds which are not urethane alcohols in a continuous manner together with one or more alkylene oxides.

Variant C) ("Continuous CAOS Procedure"):

In a further preferred embodiment of the process of the invention (variant C), an H-functional starter polyol S-I and a portion of the double metal cyanide catalyst are initially charged, and then at least one urethane alcohol of formula (II) and further double metal cyanide catalyst are fed in continuously together with the alkylene oxide, with continuous withdrawal of the polyether polyol formed here from the reaction system after a preselectable mean residence time.

In variant C) of the process of the invention, the polyether polyols are prepared in a fully continuous manner. A fully continuous process for preparing alkylene oxide addition products is described in principle in WO-A-98/03571. The procedure disclosed therein is applicable to the performance of the process of the invention. In this variant, as well as one or more alkylene oxides and at least one urethane alcohol, the DMC catalyst is also fed continuously to the reactor or a reactor system under alkoxylation conditions, and the polyether polyol is withdrawn continuously from the reactor or the reactor system after a preselectable mean residence time. For startup of such a fully continuous process, a starter polyol S-I and a portion of the DMC catalyst are initially charged. Suitable starter polyols S-I for variant C) of the process of the invention are alkylene oxide addition products, for example polyether polyols, polycarbonate polyols, polyestercarbonate polyols, polyethercarbonate polyols, for example, with OH numbers in the range from 3.0 mg KOH/g to 1000 mg KOH/g, preferably from 3.0 mg KOH/g to 300 mg KOH/g, and/or a polyether polyol prepared by the process of the invention, which has been prepared separately beforehand. Preference is given to using polyether polyol prepared by the process of the invention which has previously been prepared separately as starter polyol in variant C of the process of the invention.

For example, the reactor is operated in such a way that it has been filled completely with the reaction mixture ("liquid-full" mode).

Continuous postreaction steps may follow, for example in a reactor cascade or a tubular reactor. The volatile constituents can be removed under reduced pressure and/or by stripping, as described above.

For example, in a subsequent step, the reaction mixture removed continuously, which generally has an alkylene oxide content of from 0.05% by weight to 10% by weight, may be transferred into a postreactor in which, by way of a postreaction, the content of free alkylene oxide is reduced to less than 0.05% by weight in the reaction mixture. The postreactor may be a tubular reactor, a loop reactor or a stirred tank for example. The pressure in this postreactor is preferably at the same pressure as in the reaction apparatus in which the preceding reaction step of the addition of the alkylene oxides onto urethane alcohol is performed. The temperature in the downstream reactor is preferably 50° C. to 150° C. and more preferably 80° C. to 140° C.

In particularly preferred embodiments of variants B and C of the process of the invention, the starter polyol S-I used is a polyether polyol of the invention or a polyether polyol obtainable by the process of the invention.

The present invention further provides a polyether polyol obtainable by the process of the invention.

The OH numbers of the polyether polyols obtained preferably have values of 3 mg KOH/g to 400 mg KOH/g, more preferably of 10 mg KOH/g to 200 mg KOH/g, most preferably of 20 mg KOH/g to 150 mg KOH/g. This is true irrespective of the process variant used (A, B or C).

The equivalent molar mass is understood to mean the total mass of the material containing active hydrogen atoms divided by the number of active hydrogen atoms. In the case of materials containing hydroxyl groups, it is in the following relationship with the OH number:

equivalent molar mass=56 100/OH number[mg KOH/g]

It is optionally possible to add ageing stabilizers, for example antioxidants, to the polyether polyols obtainable by the process according to the invention.

The present invention further relates to the use of a polyether polyol of the invention for preparation of a polyurethane polymer, preferably a flexible polyurethane foam, more preferably a flexible slabstock polyurethane foam or a flexible molded polyurethane foam.

The present invention further provides a polyurethane polymer, preferably a flexible polyurethane foam, more preferably a flexible slabstock polyurethane foam or a flexible molded polyurethane foam, obtainable by reacting a polyisocyanate with a polyether polyol of the invention by a method familiar to the person skilled in the art, with the aid of standard additives, for example activators, stabilizers, blowing agents, crosslinkers, chain extenders and/or fillers, and optionally further polyether polyols, polyester polyols, polyethercarbonate polyols, polycarbonate polyols and/or filler-containing polyols (polymer polyols, polyurea dispersions, etc.).

Suitable polyisocyanates are aliphatic, cycloaliphatic, araliphatic, aromatic and heterocyclic polyisocyanates, as described, for example, by W. Siefken in Justus Liebigs Annalen der Chemie, 562, pages 75 to 136, for example those of the formula (XI)

$$Q(NCO)_n, \quad (XI)$$

in which
n=2-4, preferably 2-3,
and
Q is an aliphatic hydrocarbyl radical having 2-18 and preferably 6-10 carbon atoms, a cycloaliphatic hydrocarbyl radical having 4-15 and preferably 6-13 carbon atoms or an araliphatic hydrocarbyl radical having 8-15 and preferably 8-13 carbon atoms.

For example, the polyisocyanates are those as described in EP 0 007 502 A1, pages 7-8. Preference is generally given to the readily industrially available polyisocyanates, for example tolylene 2,4- and 2,6-diisocyanate and any desired mixtures of these isomers ("TDI"); polyphenylpolymethylene polyisocyanates as prepared by aniline-formaldehyde condensation and subsequent phosgenation ("crude MDI"), and polyisocyanates having carbodiimide groups, urethane groups, allophanate groups, isocyanurate groups, urea groups or biuret groups ("modified polyisocyanates"), especially those modified polyisocyanates which derive from tolylene 2,4- and/or 2,6-diisocyanate or from diphenylmethane 4,4'- and/or 2,4'-diisocyanate. The polyisocyanates containing urethane groups (prepolymers) may, for example, be reaction products of the polyisocyanates with polyester polyols or else any other polyols (for example conventional polyether polyols). The polyisocyanate used is preferably at least one compound selected from the group consisting of tolylene 2,4- and 2,6-diisocyanate, diphenylmethane 4,4'- and 2,4'- and 2,2'-diisocyanate and polyphenylpolymethylene polyisocyanate ("multiring MDI"); the polyisocyanate used is more preferably a mixture comprising diphenylmethane 4,4'-diisocyanate and diphenylmethane 2,4'-diisocyanate and polyphenylpolymethylene polyisocyanate.

As well as the aforementioned polyisocyanates, it is additionally also possible to use conventional polyether polyols for the preparation of the polyurethane polymers. Conventional polyether polyols in the context of the invention are understood to mean the alkylene oxide addition products of starter compounds having Zerewitinoff-active hydrogen atoms. Examples of such polyether polyols are known to those skilled in the art. They may have a hydroxyl number to DIN 53240 of ≥3.0 mg KOH/g to ≤1000 mg KOH/g, preferably of ≥5.0 mg KOH/g to ≤600 mg KOH/g. The starter compounds having Zerewitinoff-active hydrogen atoms used for the preparation of the conventional polyether polyols usually have functionalities of 2 to 8. The starter compounds may be hydroxy-functional and/or amino-functional. Examples of hydroxy-functional starter compounds are propylene glycol, ethylene glycol, diethylene glycol, dipropylene glycol, butane-1,2-diol, butane-1,3-diol, butane-1,4-diol, hexanediol, pentanediol, 3-methylpentane-1,5-diol, dodecane-1,12-diol, glycerol, trimethylolpropane, triethanolamine, pentaerythritol, sorbitol, sucrose, hydroquinone, catechol, resorcinol, bisphenol F, bisphenol A, 1,3,5-trihydroxybenzene, methylol-containing condensates of formaldehyde and phenol or melamine or urea. Examples of amino-functional starter compounds are ammonia, ethanolamine, diethanolamine, triethanolamine, isopropanolamine, diisopropanolamine, ethylenediamine, hexamethylenediamine, aniline, the isomers of toluidine, the isomers of diaminotoluene, the isomers of diaminodiphenylmethane, and higher polycyclic products obtained in the condensation of aniline with formaldehyde to give diaminodiphenylmethane.

Suitable alkylene oxides for the conventional polyether polyols are, for example, ethylene oxide, propylene oxide, 1,2-butylene oxide or 2,3-butylene oxide and styrene oxide. Preference is given to feeding propylene oxide and ethylene oxide into the reaction mixture individually, in a mixture or successively. If the alkylene oxides are metered in successively, the products produced contain polyether chains having block structures. Products having ethylene oxide end blocks are characterized, for example, by elevated concentrations of primary end groups which impart advantageous isocyanate reactivity to the systems.

The preparation of the conventional polyether polyols may be base-catalyzed, for example via alkali metal hydroxide or amine catalysis, double metal cyanide-catalyzed, or acid-catalyzed by Lewis or Brønsted acids.

As well as the aforementioned conventional polyether polyols, it is additionally or alternatively also possible to use polyester polyols for the preparation of the polyurethane polymers. Suitable polyester polyols preferably have OH numbers in the range from 6 to 800 mg KOH/g and can be prepared, for example, from polyfunctional carboxylic acids, preferably organic dicarboxylic acids having 2 to 12 carbon atoms, and polyhydric alcohols, preferably diols, having 2 to 12 carbon atoms, preferably 2 to 6 carbon atoms, by known methods. Rather than the polyfunctional carboxylic acids, it is also possible to use derivatives thereof, for example acid chlorides or anhydrides.

EXAMPLES

Test Methods

Experimentally determined OH numbers were determined by the method of DIN 53240.

The amine numbers (NH number) were determined by the method of DIN 53176.

The viscosities were determined by means of a rotary viscometer (Physica MCR 51, manufacturer: Anton Paar) by the method of DIN 53018.

The determination of the functionality of the starter in the finished polyether polyol was conducted by means of $^{13}$C NMR (from Bruker, Advance 400, 400 MHz; wait time d1: 4 s, 6000 scans). Each sample was dissolved in deuterated acetone-D6 with addition of chromium(III) acetylacetonate. The solution concentration was 500 mg/mL.

The relevant resonances in the $^{13}$C NMR (based on CHCl$_3$=7.24 ppm) are as follows:

The carbon signals of the carbon atoms bonded directly to the nitrogen (methylene groups, methine group) of the starter are evaluated:
Bifunctionally started: 40.4 ppm to 40.0 ppm (one carbon)
Trifunctionally started: 42.2 ppm to 40.5 ppm (two carbons)

Bifunctionally started means that only the OH groups of the urethane alcohol starter compound are alkoxylated.

Trifunctionally started means that the OH groups and the NH group of the urethane bond of the urethane alcohol starter compound are alkoxylated.

The chemical shifts in the $^{13}$C NMR were determined by comparative measurements (comparative spectra).

The apparent densities were determined to DIN EN ISO 845.

The compression hardnesses (40% compression) were determined to DIN EN ISO 1798.

Raw Materials Used:
Catalyst for the Alkylene Oxide Addition (DMC Catalyst):

Double metal cyanide catalyst, containing zinc hexacyanocobaltate, tert-butanol and polypropylene glycol having a number-average molecular weight of 1000 g/mol, according to example 6 in WO-A 01/80994.

Cyclic propylene carbonate (cPC): from Acros, art. no.: 131560025

Cyclic ethylene carbonate (cEC): from Acros, art. no.: 118410010

Ethanolamine: from Merck; art. no.: 800849

Stabilizer 1: siloxane-based foam stabilizer, Tegostab® BF 2370, Evonik Goldschmidt Isocyanate 1: mixture of 80% by weight of tolylene 2,4- and 20% by weight of tolylene 2,6-diisocyanate, available under the Desmodur® T 80 name, Bayer MaterialScience AG Catalyst 1: bis(2-dimethylaminoethyl) ether in dipropylene glycol, available as Addocat® 108, from Rheinchemie Catalyst 2: tin(II) ethylhexanoate, available as Dabco® T-9, from Air Products

Preparation of Urethane Alcohols

Example 1a

A 10 L four-neck flask having a reflux condenser and thermometer was initially charged with cyclic propylene carbonate (6080 g, 59.6 mol). Subsequently, ethanolamine (2405 g, 39.6 mol) was gradually added dropwise at 60° C. within 50 min at such a rate that the temperature did not exceed 72° C. The reaction was subsequently stirred at 60° C. for a further 24 h in total. After cooling to 25° C., the urethane alcohol was obtained.

Product properties of the resulting urethane alcohol:
OH number: 507 mg KOH/g
NH number: 0.51 mg KOH/g
Viscosity (25° C.): 268 mPas

Example 1b

A portion of the product was freed of volatile constituents by means of thin-film evaporation (0.1 mbar, 120° C.).
Product Properties:
OH number: 671 mg KOH/g
NH number: 0.20 mg KOH/g
Viscosity (25° C.): 3170 mPas

Example 2

A 2 L four-neck flask with reflux condenser and thermometer was initially charged with a mixture of cyclic propylene carbonate (1181 g, 11.6 mol) and cyclic ethylene carbonate (62 g, 0.7 mol) which had been heated to 50° C. Subsequently, ethanolamine (500 g, 8.2 mol) was gradually added dropwise at 60° C. within 60 min at such a rate that the temperature did not exceed 70° C. The reaction was subsequently stirred at 60° C. for a further 15 h in total. After cooling to 25° C., the urethane alcohol was obtained.
Product Properties:
OH number: 523 mg KOH/g
NH number: 0.20 mg KOH/g
Viscosity (25° C.): 313 mPas

Example 3

A 2 L four-neck flask with reflux condenser and thermometer was initially charged with a mixture of cyclic propylene carbonate (1110 g, 10.9 mol) and cyclic ethylene carbonate (123 g, 1.4 mol) which had been heated to 50° C. Subsequently, ethanolamine (500 g, 8.2 mol) was gradually added dropwise at 60° C. within 60 min at such a rate that the temperature did not exceed 79° C. The reaction was subsequently stirred at 60° C. for a further 15 h in total. After cooling to 25° C., the urethane alcohol was obtained.
Product Properties:
OH number: 527 mg KOH/g
NH number: 0.30 mg KOH/g
Viscosity (25° C.): 295 mPas

Preparation of Polyether Polyols

Example 4

Semi-Batchwise CAOS Method

A 2 liter stainless steel pressure reactor was initially charged with 200 g of polypropylene glycol having molar mass=2000 g/mol and 36 mg of DMC catalyst under nitrogen, and heated to 130° C. Stripping was accomplished by introducing nitrogen into the reaction mixture at 130° C. for a period of 30 min and simultaneously applying a reduced pressure (in absolute terms), such that a reduced pressure of 0.1 bar (absolute) was established in the reactor. Then, at 130° C. while stirring (800 rpm), 20 g of propylene oxide were first metered into the reactor within 5 min. Subsequently, over a period of 6.5 h, 838 g of propylene oxide and 122 g of urethane alcohol from example 1a were metered into the reactor at 130° C. while stirring (800 rpm). Finally, at 130° C. while stirring (800 rpm), a further 20 g of propylene oxide were metered into the reactor within 30 min. After a postreaction time of 30 min at 130° C., volatile constituents were distilled off under reduced pressure at 50 mbar (absolute) and 130° C. for 60 minutes and then the reaction mixture was cooled to room temperature.

Product Properties:
OH number: 53.3 mg KOH/g
Viscosity (25° C.): 749 mPas

Example 5

Semi-Batchwlse CAOS Method

A 2 liter stainless steel pressure reactor was initially charged with 200 g of polypropylene glycol having molar mass=2000 g/mol and 36 mg of DMC catalyst under nitrogen, and heated to 130° C. Stripping was accomplished by introducing nitrogen into the reaction mixture at 130° C. for a period of 30 min and simultaneously applying a reduced pressure (in absolute terms), such that a reduced pressure of 0.1 bar (absolute) was established in the reactor. Then, at 130° C. while stirring (800 rpm), 20 g of propylene oxide were first metered into the reactor within 5 min. Subsequently, over a period of 7 h, 876 g of propylene oxide and 84 g of urethane alcohol from example 1b were metered into the reactor at 130° C. while stirring (800 rpm). Finally, at 130° C. while stirring (800 rpm), a further 20 g of propylene oxide were metered into the reactor within 10 min. After a postreaction time of 30 min at 130° C., volatile constituents were distilled off under reduced pressure at 50 mbar (absolute) and 130° C. for 60 minutes and then the reaction mixture was cooled to room temperature.

Product Properties:
OH number: 44.5 mg KOH/g
Viscosity (25° C.): 764 mPas

Example 6

Semi-Batchwise CAOS Method

A 2 liter stainless steel pressure reactor was initially charged with 200 g of polypropylene glycol having molar mass=2000 g/mol and 36 mg of DMC catalyst under nitrogen, and heated to 130° C. Stripping was accomplished by introducing nitrogen into the reaction mixture at 130° C. for a period of 30 min and simultaneously applying a reduced pressure (in absolute terms), such that a reduced pressure of 0.1 bar (absolute) was established in the reactor. Then, at 130° C. while stirring (800 rpm), 20 g of propylene oxide were first metered into the reactor within 5 min. Subsequently, over a period of 6.5 h, 838 g of propylene oxide and 122 g of urethane alcohol from example 2 were metered into the reactor at 130° C. while stirring (800 rpm). Finally, at 130° C. while stirring (800 rpm), a further 20 g of propylene oxide were metered into the reactor within 10 min. After a postreaction time of 30 min at 130° C., volatile constituents were distilled off under reduced pressure at 50 mbar (absolute) and 130° C. for 60 minutes and then the reaction mixture was cooled to room temperature.

Product Properties:
OH number: 49.3 mg KOH/g
Viscosity (25° C.): 641 mPas

Example 7

Semi-Batchwise CAOS Method

A 2 liter stainless steel pressure reactor was initially charged with 200 g of polypropylene glycol having molar mass=2000 g/mol and 36 mg of DMC catalyst under nitrogen, and heated to 130° C. Stripping was accomplished by introducing nitrogen into the reaction mixture at 130° C. for a period of 30 min and simultaneously applying a reduced pressure (in absolute terms), such that a reduced pressure of 0.1 bar (absolute) was established in the reactor. Then, at 130° C. while stirring (800 rpm), 20 g of propylene oxide were first metered into the reactor within 5 min. Subsequently, over a period of 7 h, 838 g of propylene oxide and 122 g of urethane alcohol from example 3 were metered into the reactor at 130° C. while stirring (800 rpm). Finally, at 130° C. while stirring (800 rpm), a further 20 g of propylene oxide were metered into the reactor within 10 min. After a postreaction time of 30 min at 130° C., volatile constituents were distilled off under reduced pressure at 50 mbar (absolute) and 130° C. for 60 minutes and then the reaction mixture was cooled to room temperature.

Product Properties:
OH number: 49.9 mg KOH/g
Viscosity (25° C.): 677 mPas

Example 8

Semi-Batchwise CAOS Method, "P2P"

A 2 liter stainless steel pressure reactor was initially charged with 200 g of the polyether polyol from example 6 and 30 mg of DMC catalyst under nitrogen, and heated to 130° C. Stripping was accomplished by introducing nitrogen into the reaction mixture at 130° C. for a period of 30 min and simultaneously applying a reduced pressure (in absolute terms), such that a reduced pressure of 0.1 bar (absolute) was established in the reactor. Then, at 130° C. while stirring (800 rpm), 20 g of propylene oxide were first metered into the reactor within 5 min. Subsequently, over a period of 7 h, 838 g of propylene oxide and 122 g of urethane alcohol from example 2 were metered into the reactor at 130° C. while stirring (800 rpm). Finally, at 130° C. while stirring (800 rpm), a further 20 g of propylene oxide were metered into the reactor within 10 min. After a postreaction time of 30 min at 130° C., volatile constituents were distilled off under reduced pressure at 50 mbar (absolute) and 130° C. for 60 minutes and then the reaction mixture was cooled to room temperature.

Product Properties:
OH number: 53.6 mg KOH/g
Viscosity (25° C.): 635 mPas

Example 9

Continuous CAOS Method

The following components were metered, at 130° C. while stirring (800 rpm) over a period of 24 h, at the dosage rates specified, into a continuous 2 liter stainless steel pressure reactor operated in "liquid-full" mode (i.e. the reactor is completely filled with the reaction mixture), which had been initially charged with 2000 g of a trifunctional poly(oxypropylene) polyol having molar mass 3500 g/mol containing 25 ppm of activated DMC catalyst:

propylene oxide at 797 g/h ethylene oxide at 97 g/h mixture of 58 g of urethane alcohol from example 1a and 48 mg of DMC catalyst at 58 g/h.

The reaction mixture was withdrawn continuously from the reactor via a product discharge line and transferred to a 1 liter tubular postreactor heated to 130° C. to complete the reaction. Volatile constituents were distilled out of the reaction mixture obtained under reduced pressure at 50 mbar (absolute) and 130° C. for 60 minutes, and then it was cooled to room temperature.

A sample taken after a reaction time of 24 h was analyzed.

Product Properties:

OH number: 31.4 mg KOH/g

Viscosity (25° C.): 1302 mPas

OH functionality: about 2.9 (determined by means of $^{13}$C NMR)

Example 10

Continuous CAOS Method

The following components were metered, at 130° C. while stirring (800 rpm) over a period of 24 h, at the dosage rates specified, into a continuous 2 liter stainless steel pressure reactor operated in "liquid-full" mode (i.e. the reactor is completely filled with the reaction mixture), which had been initially charged with 200 g of the polyether polyol from example 4:

propylene oxide at 488 g/h ethylene oxide at 61 g/h mixture of 81 g of urethane alcohol from example 1a and 32 mg of DMC catalyst at 81 g/h.

The reaction mixture was withdrawn continuously from the reactor via a product discharge line and transferred to a 1 liter tubular postreactor heated to 130° C. to complete the reaction. Volatile constituents were distilled out of the reaction mixture obtained under reduced pressure at 50 mbar (absolute) and 130° C. for 60 minutes, and then it was cooled to room temperature.

A sample taken after a reaction time of 24 h was analyzed.

Product Properties:

OH number: 59.0 mg KOH/g

Viscosity (25° C.): 549 mPas

Production of Flexible Polyurethane Foams

Examples 11 & 12

Polyether Polyols from Example 8 ("P2P CAOS") and Example 10 ("Continuous CAOS")

Polyurethane foams were produced according to the recipes specified in the table below. The proportions of the components are listed in parts by weight. High-quality flexible foams having homogeneous cell structure were obtained, which were characterized by determining the apparent densities and compression hardnesses.

TABLE 1

Preparation of flexible polyurethane foams

| | Example | | | |
|---|---|---|---|---|
| | 11a | 11b | 12a | 12b |
| Polyol from example 8 | 100 | 100 | — | — |
| Polyol from example 10 | — | — | 100 | 100 |
| Stabilizer 1 | 2.4 | 1.2 | 2.4 | 1.2 |
| Catalyst 1 | 0.15 | 0.12 | 0.15 | 0.12 |
| Catalyst 2 | 0.14 | 0.18 | 0.14 | 0.18 |
| Water | 2.50 | 4.50 | 2.50 | 4.50 |
| Isocyanate 1 | 35.1 | 55.9 | 35.5 | 56.3 |
| NCO index | 108 | 108 | 108 | 108 |
| Apparent density (kg/m$^3$) | 36.6 | 24.1 | 37.0 | 24.1 |
| Compression hardness, 4th cycle (kPa) | 2.8 | 2.6 | 2.9 | 3.5 |

The invention claimed is:

1. A process for preparing polyether polyols comprising adding of alkylene oxides onto H-functional starter compounds, wherein at least one urethane alcohol of formula (II)

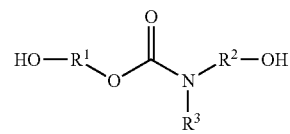

(II)

where

R$^1$ is linear or branched C$_2$- to C$_{24}$-alkylene which may optionally be interrupted by heteroatoms such as O, S or N and may be substituted, R$^2$ is linear or branched C$_2$- to C$_{24}$-alkylene which may optionally be interrupted by heteroatoms such as O, S or N and may be substituted, R$^3$ is H, linear or branched C$_1$- to C$_{24}$-alkyl, C$_3$- to C$_{24}$-cycloalkyl, C$_4$- to C$_{24}$-aryl, C$_5$- to C$_{24}$-aralkyl, C$_2$- to C$_{24}$-alkenyl, C$_2$- to C$_{24}$-alkynyl, each of which may optionally be interrupted by heteroatoms such as O, S or N and/or each of which may be substituted by alkyl, aryl and/or hydroxyl, is used as H-functional starter compound.

2. The process as claimed in claim 1, wherein
R$^1$=CH$_2$—CH$_2$ or CH$_2$—CH(CH$_3$),
R$^2$=CH$_2$—CH$_2$ or CH$_2$—CH(CH$_3$), and
R$^3$=H.

3. The process as claimed in claim 1, wherein the urethane alcohol is obtained by reacting propylene carbonate and/or ethylene carbonate with an alkanolamine of formula (III)

HN(R$^3$)—R$^2$—OH  (III)

where R$^2$ and R$^3$ are as defined in claim 1.

4. The process as claimed in claim 3, wherein the urethane alcohol is obtained by reacting propylene carbonate and/or ethylene carbonate with at least one amine selected from the group consisting of ethanolamine, diethanolamine, (N-methyl)ethanolamine, isopropanolamine, diisopropanolamine and propanolamine.

5. The process as claimed in claim 1, wherein the alkylene oxide is at least one alkylene oxide selected from the group consisting of ethylene oxide and propylene oxide.

6. The process as claimed in claim 1, wherein the addition is effected in the presence of at least one DMC catalyst.

7. The process as claimed in claim 6, wherein at least one urethane alcohol of the formula (II) and the double metal cyanide catalyst are first initially charged and then the alkylene oxide is added.

8. The process as claimed in claim 1, wherein one or more urethane alcohols of the formula (II) are metered continuously into the reactor as H-functional starter substance(s) during the reaction.

9. The process as claimed in claim 6, wherein an H-functional starter polyol S-I and the double metal cyanide catalyst are initially charged and then at least one urethane alcohol of the formula (II) is metered in continuously together with one or more alkylene oxides, wherein the H-functional starter polyol S-I has an OH number in the range from 3 mg KOH/g to 1000 mg KOH/g, and wherein the resulting reaction mixture is removed continuously from the reactor after a pre-selectable mean residence time.

10. The process as claimed in claim 8, wherein DMC catalyst is additionally also metered continuously into the reactor and the resulting reaction mixture is removed continuously from the reactor.

11. The process as claimed in claim 9, wherein the reaction mixture removed continuously from the reactor with a content of 0.05% by weight to 10% by weight of alkylene oxide is transferred into a postreactor in which, by way of a postreaction, the content of free alkylene oxide is reduced to less than 0.05% by weight in the reaction mixture.

12. The process as claimed in claim 9, wherein the starter polyol S-I used is a polyether polyol containing a structural unit of the formula (IV)

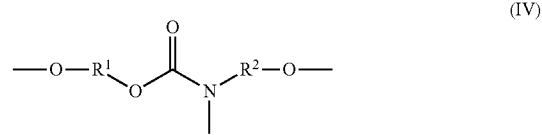

(IV)

where $R^1$ is linear or branched $C_2$- to $C_{24}$-alkylene which may optionally be interrupted by heteroatoms such as O, S or N and may be substituted, $R^2$ is linear or branched $C_2$- to $C_{24}$-alkylene which may optionally be interrupted by heteroatoms such as O, S or N and may be substituted, or a polyether polyol obtained by adding of alkylene oxides onto H-functional starter compounds, wherein at least one urethane alcohol of formula (II) used as H-functional starter compounds.

* * * * *